(12) United States Patent
Takayanagi et al.

(10) Patent No.: US 7,887,623 B2
(45) Date of Patent: Feb. 15, 2011

(54) APPARATUS FOR COLLECTING SMOKE AND DUST WITH A DEODORIZING FUNCTION AND A DEODORIZING AND FILTERING UNIT

(75) Inventors: Keisuke Takayanagi, Aichi (JP); Tomoyuki Suzuki, Aichi (JP); Hidenori Ikeno, Aichi (JP)

(73) Assignee: Sintokogio Ltd., Aichi (JP)

( * ) Notice: Subject to any disclaimer, the term of this patent is extended or adjusted under 35 U.S.C. 154(b) by 665 days.

(21) Appl. No.: 11/887,886

(22) PCT Filed: Apr. 17, 2006

(86) PCT No.: PCT/JP2006/308049

§ 371 (c)(1),
(2), (4) Date: Oct. 4, 2007

(87) PCT Pub. No.: WO2006/112440

PCT Pub. Date: Oct. 26, 2006

(65) Prior Publication Data

US 2009/0044705 A1 Feb. 19, 2009

(30) Foreign Application Priority Data

| Apr. 18, 2005 | (JP) | ............................. 2005-119614 |
| Jul. 28, 2005 | (JP) | ............................. 2005-218114 |
| Jul. 28, 2005 | (JP) | ............................. 2005-218115 |
| Aug. 9, 2005 | (JP) | ............................. 2005-230362 |
| Nov. 29, 2005 | (JP) | ............................. 2005-344135 |
| Nov. 29, 2005 | (JP) | ............................. 2005-344136 |

(51) Int. Cl.
*B01D 46/00* (2006.01)

(52) U.S. Cl. ............................. 96/109; 55/471; 55/472; 55/482; 55/486; 55/498; 96/134; 96/380; 96/381

(58) Field of Classification Search ........... 55/318–320, 55/323, 330, 333, 385.1, 385.4, 467, 471–473, 55/490, 492, 495, 497, 498, 499, 504, 524, 55/DIG. 5, DIG. 19, DIG. 30, 482, 486, 487; 96/380, 381, 382, 108–117, 134, 135, 153, 96/154

See application file for complete search history.

(56) References Cited

U.S. PATENT DOCUMENTS 3,708,965 A * 1/1973 Domnick ..................... 55/488

(Continued)

FOREIGN PATENT DOCUMENTS

DE 23 02 243 8/1973

(Continued)

*Primary Examiner*—Duane Smith
*Assistant Examiner*—Sonji Turner
(74) *Attorney, Agent, or Firm*—Finnegan, Henderson, Farabow, Garrett & Dunner, L.L.P.

(57) ABSTRACT

An apparatus for collecting smoke and dust with a deodorizing function which has excellent capability for maintenance and an improved deodorizing and silencing effect, the apparatus having a housing and a bulkhead having an opening and disposed in the housing to separate a space for deodorizing and filtering exhaust gas from a space for discharging exhaust gas, a vacuuming device for vacuuming exhaust gas disposed in the space for discharging and communicating with the opening of the bulkhead, a filtering device for filtering exhaust gas disposed in the space for deodorizing and filtering and communicating with the vacuuming device through the opening of the bulkhead, and a deodorizing device for deodorizing the exhaust gas concentrically disposed at an outer side of the filtering device.

18 Claims, 8 Drawing Sheets

U.S. PATENT DOCUMENTS

| | | | | |
|---|---|---|---|---|
| 3,850,598 A | * | 11/1974 | Boehm | 96/60 |
| 4,129,426 A | * | 12/1978 | Furasen | 96/136 |
| 4,236,902 A | * | 12/1980 | Fricke | 96/137 |
| 4,339,250 A | * | 7/1982 | Thut | 96/138 |
| 4,377,399 A | * | 3/1983 | Bryson | 96/222 |
| 4,477,270 A | * | 10/1984 | Tauch | 96/140 |
| 4,559,066 A | | 12/1985 | Hunter et al. | |
| 4,627,862 A | * | 12/1986 | Frei et al. | 96/25 |
| 4,900,346 A | * | 2/1990 | Lutz | 96/142 |
| 5,358,443 A | * | 10/1994 | Mitchell et al. | 454/230 |
| 5,641,343 A | | 6/1997 | Frey | |
| 5,753,000 A | * | 5/1998 | Chiu et al. | 55/357 |
| 5,837,020 A | * | 11/1998 | Cartellone | 55/459.3 |
| 5,997,619 A | * | 12/1999 | Knuth et al. | 96/224 |
| 6,094,774 A | * | 8/2000 | Larsen et al. | 15/326 |
| 6,152,996 A | * | 11/2000 | Linnersten et al. | 96/135 |
| 6,179,903 B1 | * | 1/2001 | Muller | 96/55 |
| 6,511,531 B1 | * | 1/2003 | Cartellone | 96/222 |
| 6,616,722 B1 | * | 9/2003 | Cartellone | 55/459.3 |
| 6,626,984 B1 | * | 9/2003 | Taylor | 96/380 |
| 7,093,773 B2 | * | 8/2006 | Kuiper | 239/57 |
| 7,470,298 B2 | * | 12/2008 | Berling et al. | 55/320 |
| 7,628,846 B2 | * | 12/2009 | Oh et al. | 96/222 |

FOREIGN PATENT DOCUMENTS

| | | |
|---|---|---|
| GB | 2 164 870 A | 4/1986 |
| JP | 63-118920 | 8/1988 |
| JP | 5-57121 | 3/1993 |
| JP | 8-57239 | 3/1996 |
| JP | 11-285611 | 10/1999 |
| JP | 2000-157823 | 6/2000 |
| JP | 2004-202392 | 7/2004 |

* cited by examiner

APPARATUS FOR COLLECTING SMOKE AND DUST WITH A DEODORIZING FUNCTION AND A DEODORIZING AND FILTERING UNIT

TECHNICAL FIELD

This invention relates to an apparatus for collecting smoke and dust with a deodorizing function and a deodorizing and filtering unit. Particularly, this invention relates to an apparatus for collecting smoke and dust with a deodorizing function and a deodorizing and filtering unit which deodorizes and collects evaporable exhaust gas that includes an odoriferous substance in addition to dust, wherein the gas and the dust are generated when products are worked by a laser-tooling machine, for example. Then, the deodorized and filtered exhaust gas is discharged to the outside of the apparatus.

BACKGROUND OF THE INVENTION

When products made from resin or rubber are worked by a laser-tooling machine, gas that includes an odoriferous substance and dust, such as fumes, is generated from the working surfaces of the products. For example, there is an apparatus disclosed in Patent Document 1 for treating exhaust gas. It discloses an apparatus comprising a blowing means for taking gaseous phase fluid into the casing of the apparatus from an intake, and for generating a flow of the gaseous phase fluid in the apparatus to discharge the fluid through an outlet, a filtering means for filtering the dust, wherein the filtering means is disposed at the upstream side of the blowing means in the pathway of the gaseous phase fluid in order to remove the dust, and a deodorizing means for deodorizing the odoriferous substance, wherein the deodorizing means is disposed at the downstream side of the blowing means in the pathway. It also discloses that the filtering means is provided with a louver made of metal and a filter made of metal, and that the deodorizing means is provided with a plurality of containers for a deodorizer for removing the odoriferous substance in gaseous fluid, which fluid is already filtered to remove the dust and is delivered by the blowing means.

However, in this conventional apparatus, since the filtering means and the deodorizing means are separately disposed in the apparatus, it is necessary to provide a space for straightening the flow of the gaseous phase fluid so as to prevent the nonuniform flow of the fluid, wherein the spaces are disposed between the filtering means and the deodorizing means and at the downstream side of the deodorizing means. Thus, since the entire apparatus becomes bigger, it becomes a problem in that a large space for installing it is required. Further, when the performance of the deodorizer of the deodorizing means is impaired by using the apparatus for a certain time, a large amount of odors accumulate in the filter made of the metal. Thus, it is required to exchange the filter and the deodorizer at the same time. Since the filtering means and the deodorizing means are separately disposed in the apparatus, it also becomes a problem in that two parts must be exchanged at the same time.

The dust taken in the casing contacts the filter made of the metal prior to contacting the deodorizing means. Thus, when the smoke and dust generated by working the products made from resin, for example, by using a laser-tooling machine, contain an odoriferous substance, the vapor of the odoriferous substance is deposited on the filter. Consequently, since the filter is easily clogged, it becomes a problem in that the life of the filter decreases. Further, the exhaust gas flows at a rate of 15-20 m/min. in the deodorizing means, to maintain a steady amount of exhaust gas to be treated. However, since the deodorizing means has a plane shape, and the flow rate of the exhaust gas is too high, it is hard for sufficient exhaust gas to pass through the deodorizer (for example, activated charcoal). Thus, it also becomes a problem in that the efficiency for deodorizing the exhaust gas is low.

Further, there are several areas of the apparatus for collecting the smoke and dust that need to be improved. Namely, they are such as to easily and quickly exchange the deodorizing and filtering unit, to improve the effect of the deodorization of the deodorizing and filtering unit without increasing the size of the unit, to reduce the noise of the apparatus for collecting the smoke and dust, and to improve the effect of the deodorization of the deodorizing and filtering unit for a specific odoriferous substance.

Patent Document 1: Japanese Patent Publication Laid-open No. 2004-202392

DISCLOSURE OF INVENTION

To solve the above problems, the apparatus for collecting smoke and dust with the deodorizing function of this invention is comprised of:

a bulkhead having an opening and disposed in the housing of the apparatus to create a separate space for deodorizing and filtering exhaust gas, wherein the space has an intake, from a space for discharging exhaust gas, wherein the space has an exhaust opening, a vacuuming means for vacuuming the exhaust gas disposed in the space for discharging and communicating with the opening of the bulkhead, a filtering means for filtering the exhaust gas disposed in the space for deodorizing and filtering and communicating with the vacuuming means through the opening of the bulkhead, wherein the filtering means has a cylindrical shape, and a deodorizing means for deodorizing the exhaust gas concentrically disposed at the outer side of the filtering means, wherein the deodorizing means has a cylindrical shape.

The apparatus for collecting smoke and dust with the deodorizing function of this invention as explained in the above paragraph is further comprised of:

a gap disposed between the inside of the deodorizing means and the outside of the filtering means, wherein the distance of the gap is 5-15 mm.

This technical feature allows the apparatus to have a decreased size and to improve the deodorizing performance.

The apparatus for collecting smoke and dust with the deodorizing function of this invention as explained in the above paragraph is further comprised of:

a control panel having an inverter controller for controlling the vacuuming means.

This technical feature allows the control panel to control the vacuuming means based on the current circumstances.

The apparatus for collecting smoke and dust with the deodorizing function of this invention is explained in the above paragraph. The deodorizing and filtering unit is comprised of the filtering means and the deodorizing means. The deodorizing and filtering unit can be supported by a fastening member that passes through the hollow of the filtering means to fix the deodorizing and filtering unit and by a guide member that is disposed along the deodorizing and filtering unit.

The fastening member is comprised of a stud bolt and a butterfly nut. The stud bolt is fixed to a installation plate at one end of it and passes through the hollow of the filtering means. The installation plate is used for connecting the vacuuming means with the bulkhead. The butterfly nut is threaded to the other end of the stud bolt.

The guide member can be comprised of two spaced guide elements with a predetermined interval between them. One end of the guide elements is fixed to the bulkhead. The other end of the guide elements is fixed to a part in the space for deodorizing and filtering the exhaust gas.

Further, the apparatus for collecting smoke and dust with the deodorizing function of this invention is comprised of:

a housing having a space for deodorizing and filtering exhaust gas and a space for discharging exhaust gas, wherein the space for deodorizing and filtering and the space for discharging are separated by a bulkhead having an opening, a deodorizing and filtering unit having a cylindrical shape, wherein the deodorizing and filtering unit is disposed near the opening of the bulkhead in the space for deodorizing and filtering, a vacuuming means for vacuuming the exhaust gas disposed near the opening of the bulkhead in the space for discharging, a control panel having an inverter controller for controlling the vacuuming means, and an acoustic absorption member for absorbing noises disposed at the inner wall of the space for discharging so that the acoustic absorption member is projected against the electrical motor of the vacuuming means.

The absorption member can be disposed at the inner wall of the space for discharging exhaust gas across the exhaust opening. It can be also formed so that it has a triangular shape. Further, it can be covered by an acoustic insulating material.

Further, the deodorizing and filtering unit can be comprised of a filtering means having a cylindrical shape, a deodorizing means concentrically disposed at the outer side of the filtering means, and cover plates disposed at both sides of the filtering means and the deodorizing means.

Further, the apparatus for collecting smoke and dust with the deodorizing function of this invention is comprised of:

a housing having a space for deodorizing and filtering exhaust gas and a space for discharging exhaust gas, wherein the space for deodorizing and filtering and the space for discharging are separated by a bulkhead having an opening, a deodorizing and filtering unit disposed near the opening of the bulkhead in the space for deodorizing and filtering, wherein the deodorizing and filtering unit has a filtering means having a cylindrical shape and a first deodorizing means concentrically disposed at the outer side of the filtering means, a vacuuming means for vacuuming the exhaust gas disposed near the opening of the bulkhead in the space for discharging, and a control panel for controlling the vacuuming means, wherein in the pathway for discharging the exhaust gas from the exhaust portion of the vacuuming means to the exhaust opening for discharging the exhaust gas to the outside of the housing, the exhaust portion is in communication with an exhaust pocket, and wherein a second deodorizing means also having a noise-absorbing function is adjacently disposed at the downstream side of the exhaust pocket.

Further, the second deodorizing means can be comprised of a two-layered structure comprising a deodorizing means and a filtering means.

Further, the deodorizing means is comprised of a perforated material forming the inner wall and the outer wall of the deodorizing means, and a deodorizer located between them. Based on this technical feature, the deodorizing means can be installed on the outer side of the filtering means so that the exhaust gas, which includes the odoriferous substance, can flow through the deodorizer.

Further, in the apparatus for collecting smoke and dust with the deodorizing function of this invention as explained above, the perforated material is a net made from a resin. Based on this technical feature, it is possible to reduce the weight of the apparatus and to easily guide the exhaust gas, which includes the odoriferous substance, so as to have it pass through the deodorizer.

Further, in the apparatus for collecting smoke and dust with the deodorizing function of this invention as explained in the above paragraph activated charcoal is used for the deodorizer. Based on this technical feature, it is possible to effectively remove the odoriferous substance which is contained in the smoke and dust.

The activated charcoal can be made from palm nuts. It is ground and has an irregular form of 1-6 mm in size, and has a specific surface area of more than 1,000 $m^2/g$. Further, the activated charcoal can be impregnated with an impregnating agent. The impregnating agent is an organic or inorganic substance that affects a specific odoriferous substance.

The deodorizing and filtering unit of this invention is comprised of a filtering means having a cylindrical shape and a deodorizing means concentrically disposed at the outer side of the filtering means. The filtering means and the deodorizing means are combined by cover plates made from metal or resin. The cover plates are disposed at the openings which are provided at both sides of the filtering means and the deodorizing means. Based on this technical feature, the deodorizing and filtering means can be easily exchanged at the same time.

The deodorizing means explained previously can be used in this unit.

It is apparent from the explanations of the above paragraphs that this invention can provide an apparatus for collecting smoke and dust with a deodorizing function which can reduce the space for installing such an apparatus, increase the life of such a filter, and improve the efficiency of such a deodorization.

According to this invention, since the filtering means and the deodorizing means are combined and integrated, the deodorizing and filtering unit can be easily and quickly exchanged.

According to this invention, since the acoustic insulating material can absorb the higher harmonic waves generated from the electric motor, which is controlled by the inverter controller, it is possible to reduce the noises that leak from the space for discharging exhaust gas.

According to this invention, since the first deodorizing means, the second deodorizing means, and the exhaust pocket can be provided in this apparatus, the deodorizing and filtering unit, which includes the first deodorizing means, can clean the exhaust gas. Then the exhaust gas treated by the first deodorizing means is discharged into the exhaust pocket, which is communicated to the exhaust portion of the vacuuming means. Next, the exhaust gas can pass through the second deodorizing means adjacently disposed at the downstream side of the exhaust pocket. Thus, it is possible to improve the efficiency of the deodorization of the apparatus.

Since the second deodorizing means is disposed at the downstream side of the exhaust pocket and placed near the vacuuming means (for example, under it), it is possible to reduce the size of the apparatus. Since the first deodorizing means, which is contained in the deodorizing and filtering unit, can reduce the noises generated in the space for deodorizing and filtering exhaust gas, and, further, since the pressure of the exhaust gas is reduced by discharging it through the exhaust pocket and the second deodorizing means, the noises of the apparatus can be considerably reduced.

By using the deodorizing means of this invention, which includes the impregnated charcoal, it is also possible to improve the efficiency of the deodorization for the specific odoriferous substance.

PREFERRED EMBODIMENTS OF THE INVENTION

Below, the preferred embodiments of the invention are explained based on the figures. In the invention, the "exhaust gas" is defined as a gas which contains fumes generated from the vapors from metal during welding or gas generated when products are worked by a laser-tooling machine, for example. These gases include an odoriferous substance, in addition to smoke and dust.

Figure 1:
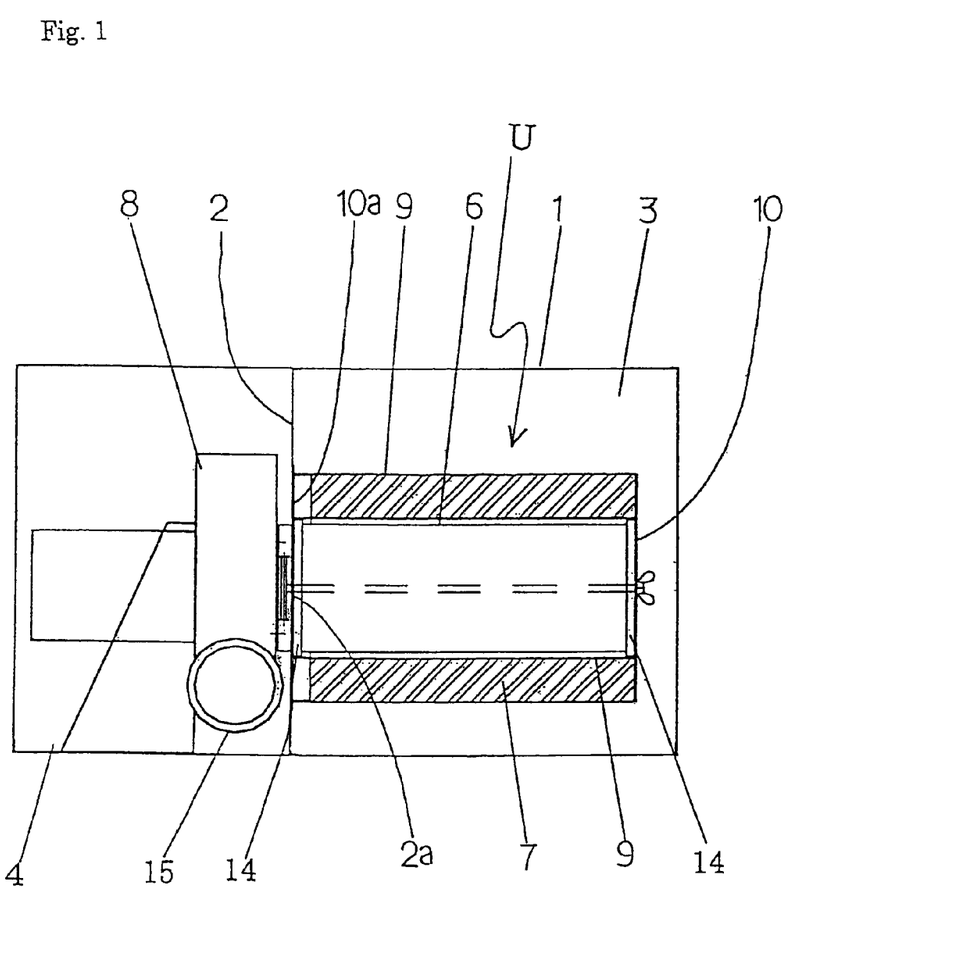
FIG. 1 shows an elevational and sectional view of an apparatus for collecting smoke and dust with the deodorizing function of embodiment 1 of the invention.
Figure 2:
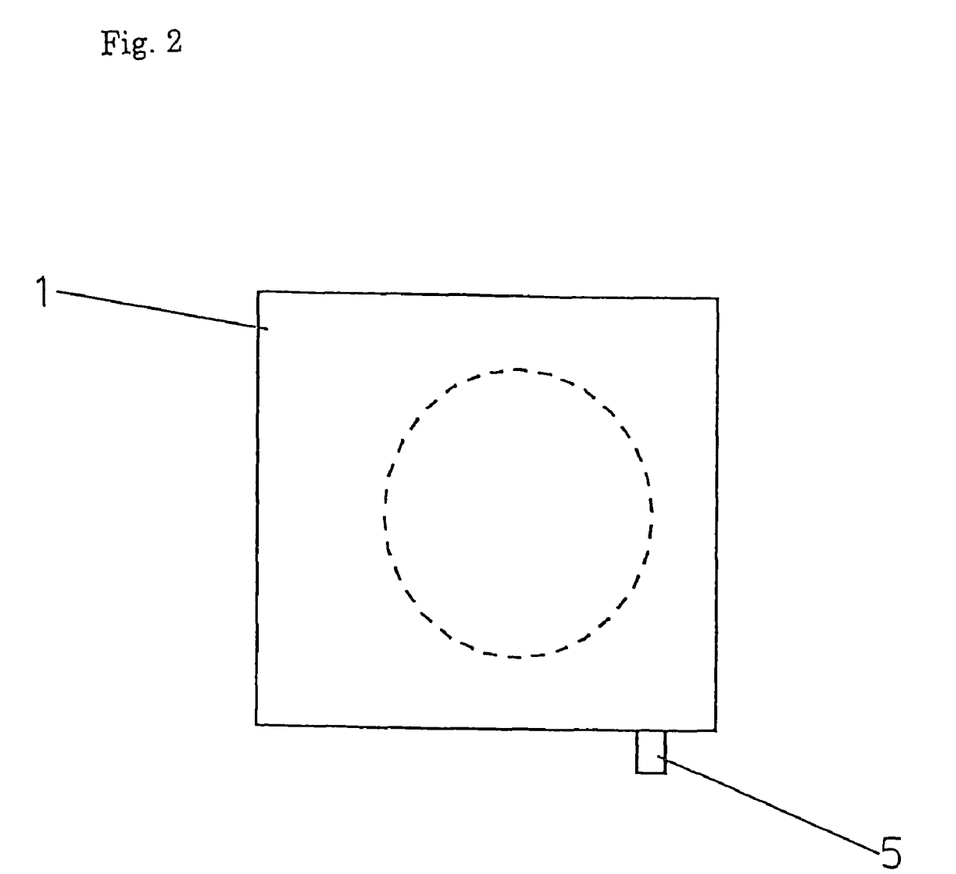
FIG. 2 shows the plane view of the apparatus for collecting smoke and dust with the deodorizing function of embodiment 1 of the invention.
Figure 3:
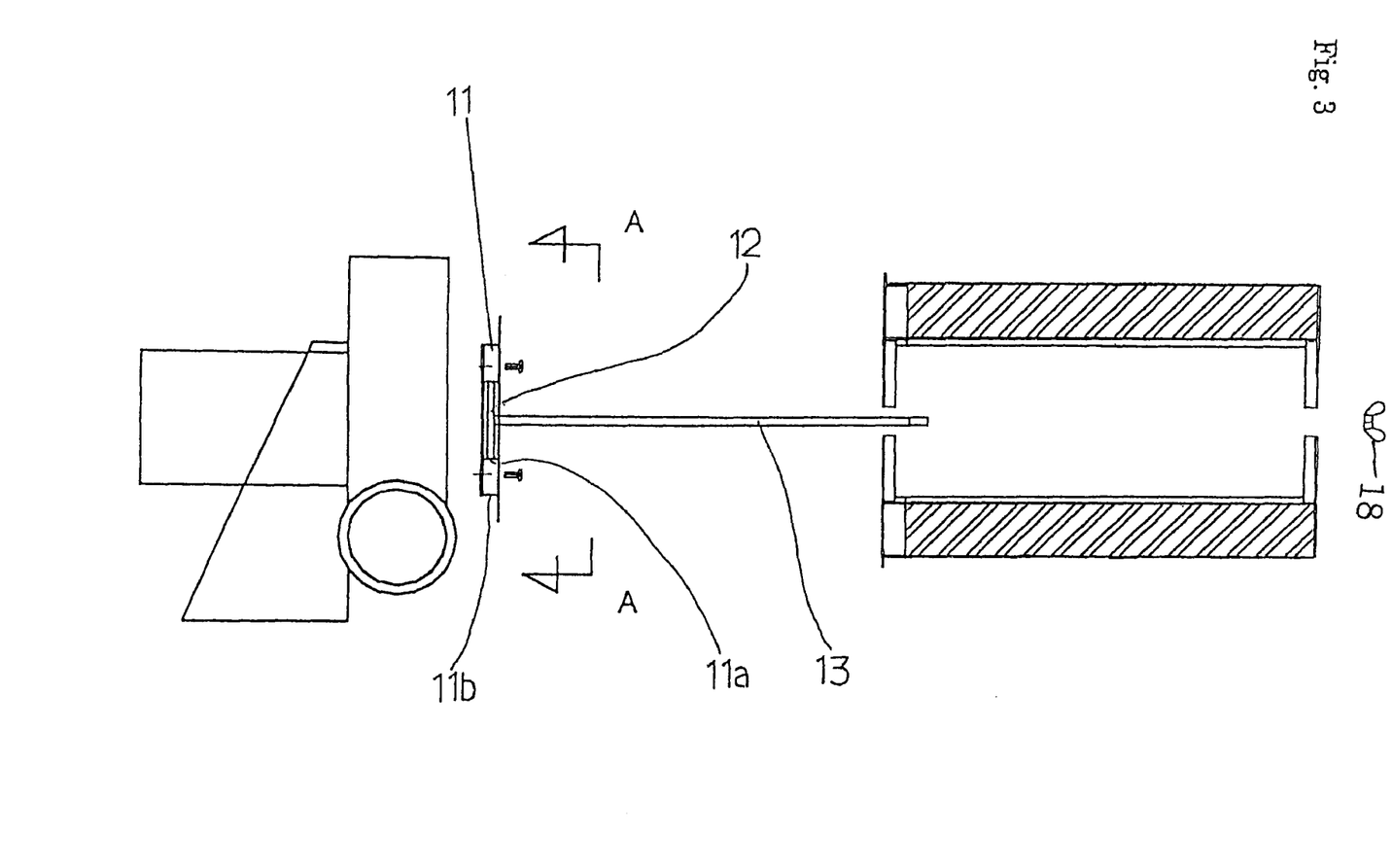
FIG. 3 shows the structure connecting the vacuuming means to the filtering means and the deodorizing means of the apparatus for collecting smoke and dust of FIG. 1.
Figure 4:
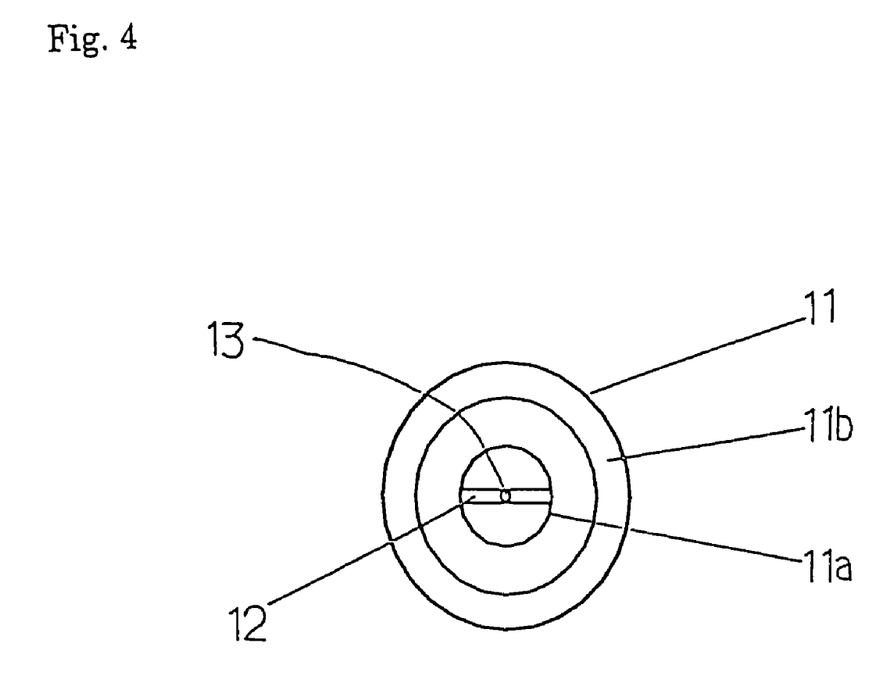
FIG. 4 shows a sectional view at line A-A of FIG. 3.
Figure 5:
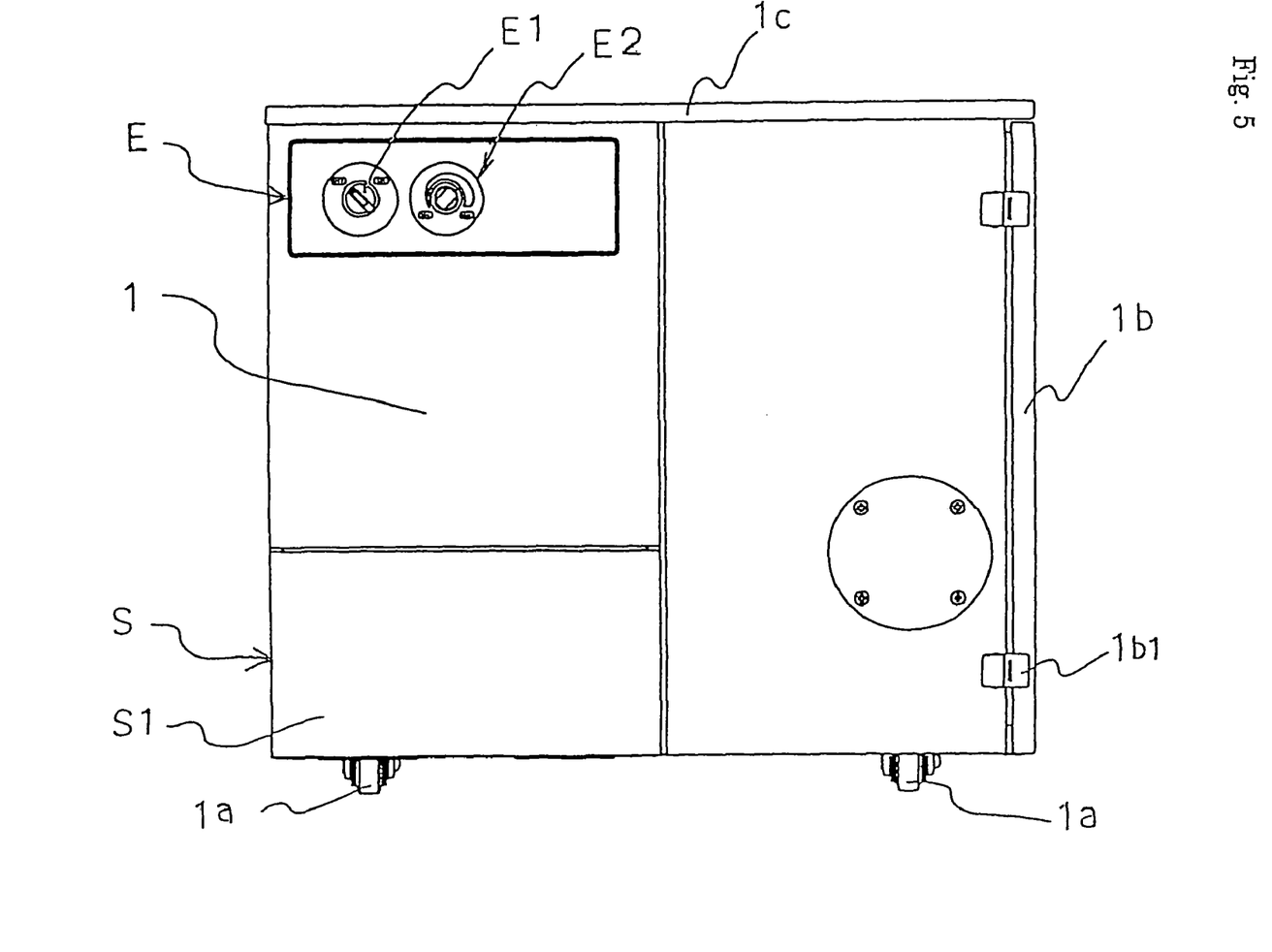
FIG. 5 shows an elevational view of an apparatus for collecting smoke and dust with the deodorizing function of the invention.

First, embodiment 1 of this invention is explained based on FIGS. 1-4. In FIGS. 1 and 2, number 1 denotes a housing having a rectangular box structure (the casing of the main body of the apparatus). The internal space of the housing 1 is separated into a space for deodorizing and filtering exhaust gas 3 and a space for discharging exhaust gas 4 by a bulkhead 2. Thus, the exhaust gas sucked into the space for deodorizing and filtering 3 must pass through a deodorizing means and a filtering means, which are explained in detail below, in order to enter the space for discharging.

An intake 5 is disposed at the side wall of the space for deodorizing and filtering 3. The exhaust gas can be sucked into the housing 1 through the intake 5. (See FIG. 2.)

In the space for deodorizing and filtering 3, a filtering means 6 for filtering the exhaust gas having a cylindrical shape is removably mounted on the bulkhead 2. One side of the filtering means 6, which has openings at both its sides, directly contacts the bulkhead 2. Further, the filtering means 6 is mounted so that the centerline of the filtering means 6 corresponds to the center of an opening 2a of the bulkhead 2. The opening 2a is located near the center of the bulkhead 2. The filtering means 6 has a cylindrical shape that has cornice-like circular folding rings. A punched metal having a cylindrical shape (not shown in the figures) is disposed at the inner surface of the filtering means 6 to strengthen its structure. Further, cover plates 14, 14 having a disk-like shape, which plates are made of a metal and formed by punching by using a pressing machine, are fixed to both sides of the filtering means 6.

A deodorizing means 7 for deodorizing the exhaust gas is concentrically disposed at an outer side of the filtering means 6. A gap with a thickness of 5-15 mm is provided between a surface of the inside of the deodorizing means and a surface of the outside of the filtering means.

If the gap were to be greater than 15 mm (for example, 20 mm), since the diameter of the deodorizing means 7 that includes the filtering means 6 would become greater, it would be difficult to reduce the size of the apparatus. In contrast, if the gap were to be smaller (for example, less than 1 mm), since the flow of the exhaust gas that flows into the filtering means 6 would become nonuniform, the efficiency of the filtering means 6 would decrease. Thus, a gap of 5-15 mm is preferable.

An air blower 8 as the vacuuming means is disposed in the space for discharging exhaust gas 4 so that the centerline of the intake of the air blower 8 corresponds to the center of the opening 2a of the bulkhead 2. Thus, the air blower 8 communicates with the filtering means 6. Consequently, the exhaust gas that flows into the housing 1 is discharged into the outer atmosphere through an exhaust port 15 disposed at the sidewall of the space for discharging exhaust gas 4.

Communicating the air blower 8 with the filtering means 6 is achieved by fastening the air blower 8 to the bottom surface of an installation plate 11. An opening is disposed at the center of the installation plate 11. The installation plate 11 has an inner wall 11a surrounding the opening and an outer wall 11b extending from the outer circumference of the bottom surface of the installation plate 11. A flange is formed at the tip of the outer wall by folding the edge of the outer wall. A fixing member 12 having a bar-like shape is mounted in the inner side of the inner wall 11a, which fixing member extends across the opening. A stud bolt as a fastening member 13, which bolt has a predetermined length that is longer than the axial length of the filtering means 6, is fixed at the center of the fixing member 12. (See FIGS. 3 and 4.)

The inner and outer walls of the deodorizing means 7 are formed by nets 9, 9 made from a resin and having an air permeability. The space between the nets is filled with activated charcoal as a deodorizer. Crushed activated charcoal having an average particle diameter of 1-10 mm can be used. However, the particle diameter of the activated charcoal must be larger than the mesh size of the nets 9, 9.

Various types of activated charcoal can be selected to be used for the deodorizing means 7. Various types of the activated charcoal of A-D were tested to evaluate the efficiency of the deodorization of them at the flow rate of the exhaust gas of 0.15 m³/min. Table 1 shows the result of the tests. As shown in Table 1, the efficiency of the deodorization of the activated charcoal made from palm nuts is higher than that of the activated charcoal made from a mineral coal. The efficiency of the deodorization of the activated charcoal that is crushed and has a nonuniform shape is higher than that of the activated charcoal that is formed so that it has particle shape. Further, the greater the specific surface area (a surface area/weight; m²/g) is of the activated charcoal, the higher the efficiency of its deodorization. Thus, the activated charcoal of C, which has the highest efficiency for deodorization, has an excellent property.

TABLE 1

| Type | Type of activated charcoal | Properties | | |
|---|---|---|---|---|
| | | Average diameter | Shape | Efficiency for deodorization |
| A | Activated charcoal made from a mineral coal | About 3 mm | Crushed | 36% |
| B | Activated charcoal made from palm nuts | About 4 mm | Crushed | 58% |
| C | Activated charcoal made from palm nuts (The specific surface area of Type C is 1.2 times greater than that of Type B.) | About 4 mm | Crushed | 64% |
| D | Activated charcoal made from palm nuts (This is made from Type B by forming it so that it has a particle shape) | About 4 mm | Particle | 51% |

The average diameter of the activated charcoal is preferably 1-6 mm. If the average diameter of the activated charcoal were to be less than 1 mm, the resistance of the exhaust-gas flow passing through the charcoal would increase. Consequently, the power that is required to drive the apparatus would increase. Accordingly, the running cost of the apparatus would be greater. The specific surface area of the activated charcoal is preferably more than 1,000 $m^2/g$.

As explained previously, since the deodorizing means 7 has a cylindrical structure, the surface of the deodorizer of it, which surface contacts the exhaust gas, is greater than that of other deodorizing means having a planar shape, for example. Thus, even if the rate of flow of the exhaust gas is low, such as 3-12 m/min., for example, it would be possible to treat a sufficient quantity of the exhaust gas. Thus, since the rate of flow of the exhaust gas can be reduced, the time while the exhaust gas is contacting the activated charcoal would increase. Consequently, since a sufficient quantity of exhaust gas can pass through the particles of the activated charcoal, the efficiency of the deodorization can be improved. Further, the life of the activated charcoal can also be improved.

As explained previously, the activated charcoal of C has the highest efficiency of deodorization. However, for the present invention, the activated charcoal is not limited to C. Activated charcoal improved for deodorizing a specific odor by impregnating it with an impregnating agent can also be used. An inorganic or organic material which can deodorize a specific odor, such as an aldehyde or ammonia, can be used as the impregnating agent. For example, bromine or iodine can be used as an inorganic impregnating agent. For example, an amine or a carboxylate can be used as an organic impregnating agent.

When the odor is not sharp or strong, a pumice stone having a diameter of 2-4 mm can be used as a deodorizer, instead of activated charcoal. In this case, the performance of the deodorizing means is not so high. However, since the pumice stone protects the surface of the filtering means 6, the life of the filtering means 6 can be improved.

For this deodorizing means 7, since it has a cylindrical structure, the surface of its deodorizer, which surface contacts the exhaust gas, is greater than that of other deodorizing means having a planar shape, for example. Thus, even if the rate of flow of the exhaust gas were to be low (3-12 m/min.), for example, it would be possible to have a treatment with a sufficient quantity of exhaust gas.

Thus, since the rate of flow of the exhaust gas can be reduced, the time while the exhaust gas is contacting the activated charcoal would increase. Consequently, since sufficient exhaust gas can pass through the particles of the activated charcoal, the efficiency of the deodorization can be improved. Further, the life of the activated charcoal can also be improved.

The life of the filtering means 6 and the deodorizing means 7 are determined as follows. Namely, the life of the filtering means 6 is determined as the time until the filter clogs with dust. Then, the life of the deodorizing means 7 is determined as the break through time of activated charcoal. It is preferable to set the surface area of the filter and the quantity of the activated charcoal so that the time until the filter is clogged with dust becomes almost equal to the break through time of the activated charcoal.

A cover plate 10 is disposed at the side of the right ends of the filtering means 6 and the deodorizing means 7 (see FIG. 1). The cover plate 10 is provided with an opening that is slightly larger than the diameter of the stud bolt 13 at its center. A cover plate 10a is also disposed at the side of the left ends of the filtering means 6 and the deodorizing means 7 (see FIG. 1). The cover plate 10a is provided with an opening that is as large as the diameter of the opening 2a of the bulkhead 2. Thus, the filtering means 6 and the deodorizing means 7 are integrated. The cover plates 10, 10a can be made from metal or resin.

For the deodorizing and filtering unit U explained above, the stud bolt 13 is disposed in the filtering means 6 through the hollow of it so that its distal end protrudes from the opening of the right cover plate 10, which has a predetermined length. Then, the stud bolt 13 is fixed to the filtering means 6 and the deodorizing means 7 by using a butterfly nut 18. Thus, it is possible to easily replace the filtering means 6 and the deodorizing means 7.

FIGS. 5-8 show embodiment 2 of an apparatus with a deodorizing function for collecting smoke and dust. The apparatus is comprised of a housing 1, a deodorizing and filtering unit U, an air blower 8 acting as a vacuuming means, and a control panel E. The apparatus can be freely moved, since casters 1a (not shown in FIG. 7) are mounted on the bottom surface of the housing 1. The housing 1 is constituted of the casing of the main body of the apparatus and has a rectangular box structure. A front panel 1b is fixed to the housing 1 by opening and closing fittings disposed at the four corners of the panel 1b so that the panel 1b can be easily removed from the housing 1. Further, an upper panel 1c is fixed to the housing 1 by magnets and fittings disposed at the upper surface of the housing 1 and the inner surface of the upper panel 1c so that the panel 1c can be easily removed from the housing 1.

Figure 6:
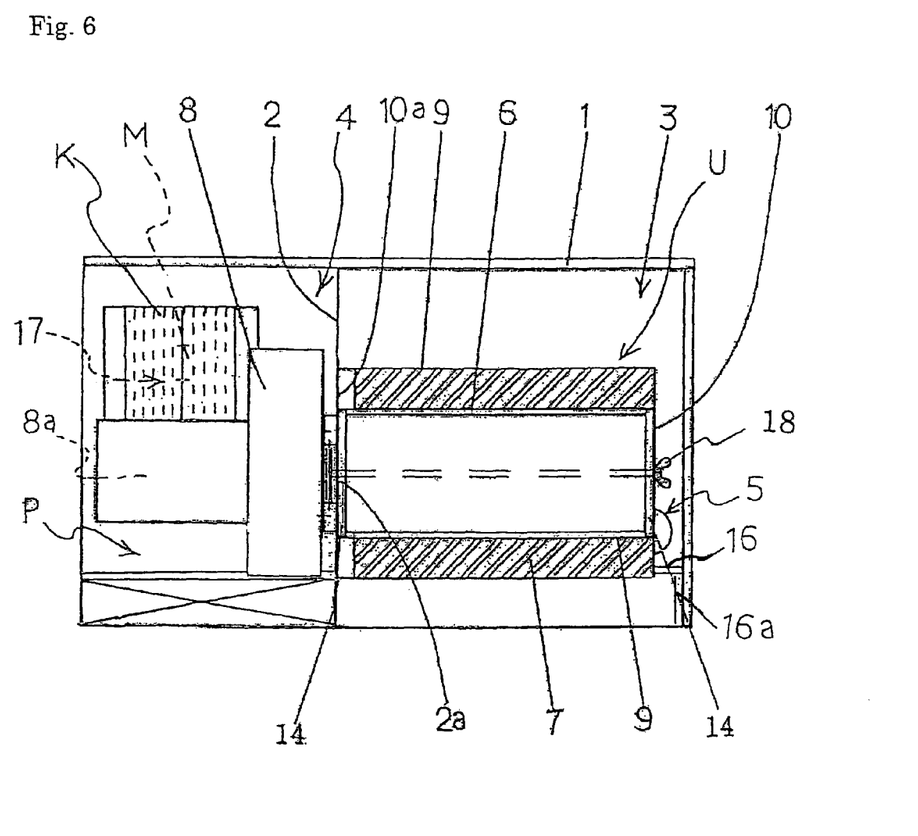
FIG. 6 shows an elevational section view of an apparatus for collecting smoke and dust with the deodorizing function of embodiment 2 of the invention.
Figure 7:
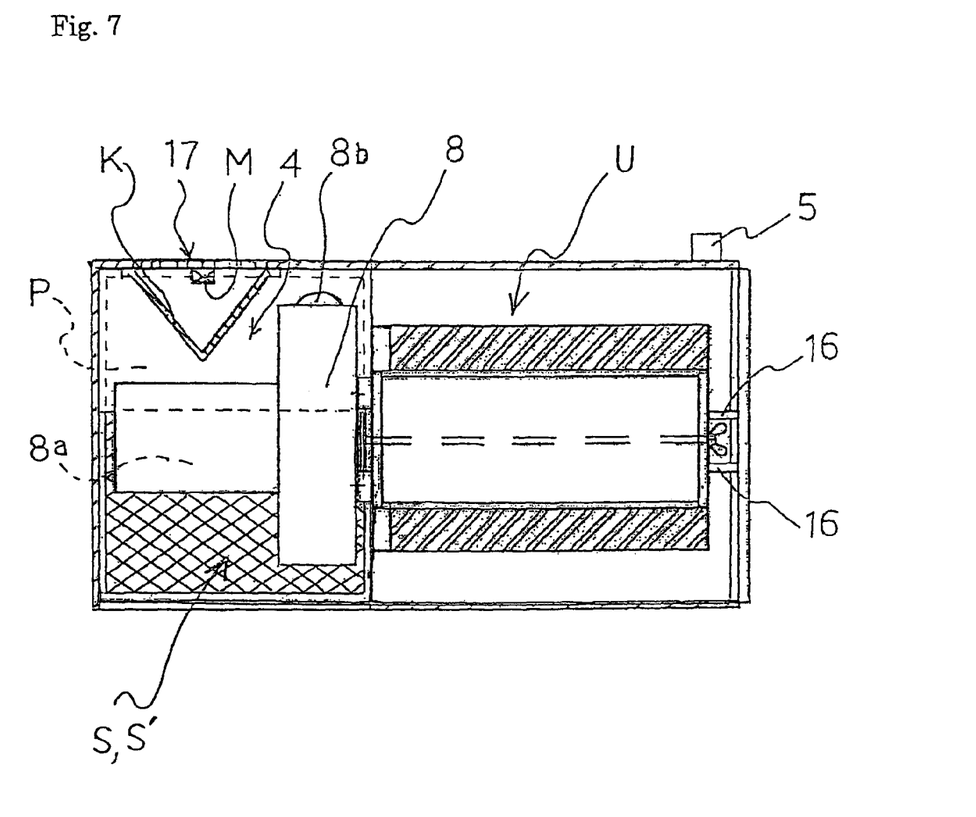
FIG. 7 shows the side sectional view of the apparatus for collecting smoke and dust with the deodorizing function of embodiment 2 of the invention.
Figure 8:
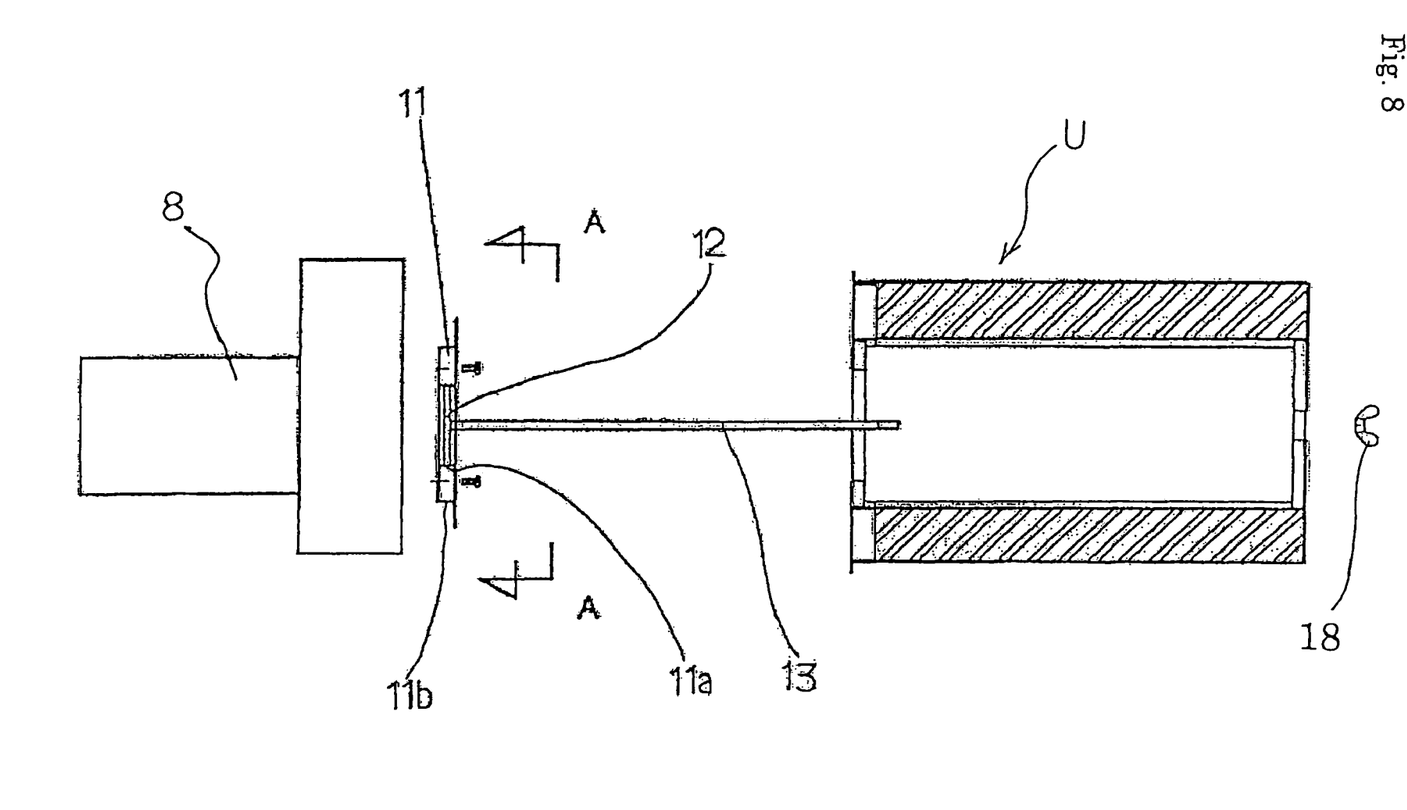
FIG. 8 shows the structure connecting an air blower to the filtering means and the deodorizing means of FIGS. 6 and 7.

The inner space of the housing 1 is divided, by the bulkhead 2 having the opening 2a, into the space for deodorizing and filtering the exhaust gas 3 and the space for discharging the exhaust gas 4. The exhaust gas taken into the space for deodorizing and filtering 3 must pass through the deodorizing means 7 and the filtering means 6 when it enters the space for discharging the exhaust gas 4.

An incombustible and acoustical insulation mat (not shown) made from a sponge is disposed at the inner wall of the space for discharging the exhaust gas 4. Further, the intake 5 is disposed at the side wall of the space for deodorizing and filtering 3. The exhaust gas can be taken into the housing 1 through the intake 5 (see FIG. 7).

The control panel E is provided with an electrical power switch E1 and a knob E2 for controlling the speed of the revolutions of the air blower 8 so as to control it by an inverter controller. For the apparatus for collecting smoke and dust of embodiment 2, the apparatus can be driven by switching the electrical power switch E1. Further, the apparatus can be operated so that it is activated simultaneously with other processing machines.

As shown in FIGS. 6 and 7, an acoustic absorption member K forming openings at an upper and a lower end of the absorption member is disposed at the inner wall of the housing 1 so that it is laid across an exhaust opening 17. The acoustic absorption member K has a V-shaped configuration and protrudes toward a driving motor 8a of the air blower 8. Since the acoustic absorption member K can absorb higher harmonic noises generated from the driving motor 8a controlled by the inverter controller, the noises generated in the space for discharging exhaust gas 4 can be reduced. For this embodiment, it is explained that the acoustic absorption member K has the V-shaped configuration and is laid across the exhaust opening 17. However, the shape and disposition of the acoustic absorption member K are not limited to these. It is also possible for the acoustic absorption member K to have a curved configuration and to be disposed at an arbitrary position on the inner wall of the space for discharging exhaust gas 4. Further, the incombustible and acoustical insulation mat made from a sponge can be disposed on the acoustic absorption member K.

The deodorizing and filtering unit U of embodiment 2 is the same as that explained in embodiment 1. For embodiment 2 as well as embodiment 1, the stud bolt 13, which constitutes a fastening member, is disposed in the filtering means 6 through the hollow of it so that its distal end protrudes from the opening of the right cover plate 10 with a predetermined length. Then, the stud bolt 13 is fixed to the deodorizing means 7 and the filtering means 6 by a butterfly nut 18.

Further, for embodiment 2, two spaced guide elements 16 are disposed at the inner wall of the housing 1 to guide and support the deodorizing and filtering unit U. The guide elements 16 are arranged with a predetermined interval between them and along the deodorizing and filtering unit U. For example, one end of the guide elements 16 is fixed to the bulkhead 2, and the other ends of them are fixed to a structure 16a placed at the bottom of the housing 1. Thus, the deodorizing and filtering unit U is supported by fastening member 13 and two guide elements 16.

For embodiment 2, it is explained that the deodorizing and filtering unit U is supported by the fastening member, which is constituted of the stud bolt 13, the butterfly nut 18, and two guide members 16. However, the structure to support the deodorizing and filtering unit U is not limited to this. For example, it is possible to support the air blower 8 and the deodorizing and filtering unit U by using the threaded portion formed on them.

When the deodorizing and filtering unit U is to be replaced, it is easy to do so by removing the butterfly nut 18, and then taking the deodorizing and filtering unit U out along the stud bolt 13 and the two guide members 16 disposed under the deodorizing and filtering unit U. All components of the deodorizing and filtering unit U explained in this embodiment, such as the cylindrical member having many holes, the installation plate, and the cover plates, can be made from resin. Consequently, it is possible to scrap the deodorizing and filtering unit U without any disassembly.

For the two embodiments explained previously, since the apparatus for collecting smoke and dust with a deodorizing function has the above configuration, the exhaust gas is taken into the space for deodorizing and filtering 3 in the housing 1 by the air blower 8 through the intake 5. The exhaust gas flows into the filtering means 6 through the deodorizing means 7 with a uniform flow rate over the entire surface of the deodorizing means 7, since the exhaust gas circulates around the deodorizing means 7 (such a circulating flow is caused by the air blower 8). Thus, the exhaust gas is efficiently deodorized and filtered by the entire surface of the deodorizing means 7 and the filtering means 6. Further, the noises generated in the space for deodorizing and filtering 3 can also be reduced by the deodorizing means 7.

Namely, the exhaust gas taken into the space for deodorizing and filtering 3 enters the activated charcoal acting as a deodorizer through the small mesh of the nets 9, 9 made from a resin. The exhaust gas is deodorized when it passes through the activated charcoal. The deodorized exhaust gas passing through the activated charcoal is also filtered by the filtering means 6. At that time, since fumes and dust are filtered out, only the clean air passes through the air blower 8. Then the clean air is discharged into the atmosphere around the apparatus through the pathway of the exhaust gas, which includes the exhaust opening 17 in the space for discharging exhaust gas 4.

For embodiment 2, as shown in FIGS. 6 and 7, the exhaust pocket P, which communicates with the exhaust portion 8b of the air blower 8, can be disposed in the pathway of the exhaust gas. A muffling portion S can also be disposed at a place adjacent to the downstream side of the exhaust pocket P, which place is located under the air blower. The muffling portion S can be freely removed from the space for discharging exhaust gas 4 or placed in it by removing the cover S1 for the muffling portion S that is fixed to the housing 1 (see FIG. 5). The muffling portion S can be made from a fibrous substance having an air permeability or a filter-like device. When the clean air passes through the muffling portion S, since the variation of the pressure of the air is suppressed, the noises caused by the exhaust gas can be reduced. Further, since the clean air passing through the muffling portion S can absorb the heat generated by the driving motor 8a for the air blower 8 while it is flowing around the air blower 8, it can cool the driving motor 8a.

In that embodiment explained above, the muffling portion S is disposed at the place adjacent to the downstream side of the exhaust pocket P, which place is located under the air blower. However, a second deodorizing means S' can be disposed, instead of the muffling portion S. (In this case, it is defined that the deodorizing means previously explained is the "first deodorizing means," and that the deodorizing means disposed instead of the muffling portion S is the "second deodorizing means.")

For this embodiment, as shown in FIGS. 6 and 7 indicating the pathway of the exhaust gas, the exhaust pocket P, which communicates with the exhaust portion 8b of the air blower 8, is disposed in the pathway of the exhaust gas. The second deodorizing means S' is also disposed at the place adjacent to the downstream side of the exhaust pocket P, which place is located under the air blower. The second deodorizing means S' can be freely removed from the space for discharging exhaust gas 4 or placed in it by removing the cover S1 for the second deodorizing means S', which cover is fixed to the housing 1 (see FIG. 5). The second deodorizing means S' can be constituted of a deodorizer accommodated in a net or a deodorizing means having a double structure, such as activated charcoal covered with a filter, for example.

The size of the second deodorizing means S' is not limited as long as it can be accommodated in the space under the air blower 8. However, it is necessary to design the size so as to reduce the velocity of the exhaust gas, so as to thereby decrease the loss of the pressure of the exhaust gas. When the clean air, which is the filtered and deodorized exhaust gas, passes through the second deodorizing means S', since the variation of the pressure of the air is suppressed, the noises caused by the exhaust gas can be reduced.

Further, since the clean air passing through the second deodorizing means S' can absorb the heat generated by the driving motor 8a for the air blower 8 while it is flowing around the air blower 8, it can cool the driving motor 8a.

For this embodiment, since the exhaust gas must pass through the first deodorizing means 7 and the second deodorizing means S', only clean air is discharged into the atmosphere around the apparatus through the pathway of the exhaust gas, which includes the exhaust opening 17 in the space for discharging the exhaust gas 4. Further, it is possible to reduce the noises of the apparatus.

Further, if it is required to increase cleanliness, it is possible to place a HEPA (HEPA: High Efficiency Air Filter; this type of filter has the capability to filter more than 99.7% of particles of 0.3 μm or more) or an ULPA (ULPA: Ultra Low Penetration Air Filter; this type of filter has the capability to filter more than 99.999% of particles of 0.1 μm or more) at the exhaust opening 17 in the space for discharging exhaust gas 4. These filters can improve the cleanliness of the exhaust gas.

Further, for this embodiment, a monitoring means M to monitor an operational condition, such as the life of the deodorizing and filtering unit or the reduction of the pressure of the exhaust gas, can be provided.

As shown in FIGS. 6 and 7, for example, the monitoring means M can be provided with an alarm and an odor sensor, such as a semiconductor-type odor sensor, to inform one that the monitoring means M is monitoring the reduction of the capability of deodorization of the deodorizing and filtering unit. If the odor sensor detects an odor to be at more than a predetermined level, the alarm will give a warning by switching on a light or sounding an alarm.

Further, the monitoring means M can be provided with an alarm and air-pressure gauges, such as a diaphragm-type pressure gauge, to inform one that the monitoring means M is monitoring the reduction of the capability of deodorization of the deodorizing and filtering unit, which reduction is caused by being clogged. The air-pressure gauges are disposed at the intake 5 of the space for deodorizing and filtering exhaust gas 3 and the exhaust opening 17 of the space for discharging exhaust gas 4.

If the air-pressure gauges detect that the difference between the measured values by the gauges disposed at the intake 5 and the exhaust opening 17 is larger than a predetermined level, the alarm would give a warning by switching on a light or sounding an alarm.

Further, the monitoring means M can be provided with an alarm and gas-flow meters, such as a venturi-type flow meter, to inform one that the monitoring means is monitoring the reduction of the capability of the deodorization of the deodorizing and filtering unit, which reduction is caused by being clogged, namely, caused by the reduction of the flow rate of the exhaust gas. The gas-flow meters are disposed at the intake 5 of the space for deodorizing and filtering the exhaust gas 3 and the exhaust opening 17 of the space for discharging the exhaust gas 4.

If the gas-flow meters detect the fact that the difference between the measured values by the gauges is greater than a predetermined level, the alarm would give a warning by switching on a light or sounding an alarm.

In these embodiments, since the monitoring means M monitors the reduction of the capability of the deodorizing and filtering unit, it becomes easy to determine the timing for replacing the deodorizing and filtering unit. Thus, it is easy to maintain the apparatus.

If the monitoring means M further comprises a transmitter for the alarm, alarm signals can be transmitted to an observation center to control the production lines of a factory.

What we claim is:

1. An apparatus for collecting smoke and dust with a deodorizing function, comprising:
   a housing having a space for deodorizing and filtering exhaust gas and a space for discharging exhaust gas, which spaces are separated by a bulkhead having an opening,
   a deodorizing and filtering unit located at the opening of the bulkhead in the space for deodorizing and filtering exhaust gas, wherein the deodorizing and filtering unit has a filtering means having a cylindrical shape and a deodorizing means concentrically disposed at an outer side of the filtering means, and
   a vacuuming means disposed at the opening of the bulkhead for pulling exhaust gas that has passed through the deodorizing and filtering unit through the opening and into the space for discharging exhaust gas,
   wherein the deodorizing and filtering unit is supported and held in the housing by a fastening member that passes through a hollow of cylindrical filtering means and two guide elements that are located in the housing along a side of the deodorizing and filtering unit.

2. The apparatus for collecting smoke and dust with a deodorizing function of claim 1, wherein there is a gap of 5-15 mm between an inside surface of the deodorizing means and an outside surface of the filtering means.

3. The apparatus for collecting smoke and dust with a deodorizing function of claim 1, wherein the vacuuming means comprises an air blower having a driving motor and further comprising a control panel having an inverter controller for controlling the driving motor of the vacuuming means.

4. The apparatus for collecting smoke and dust with a deodorizing function of claim 1, wherein the fastening member includes a stud bolt that is fixed at one end to an installation plate, which plate connects the vacuuming means to the bulkhead, and which bolt passes through the hollow of the filtering means, and a butterfly nut threaded to the other end of the stud bolt to hold the deodorizing and filtering unit in place in the housing.

5. The apparatus for collecting smoke and dust with a deodorizing function of claim 1, wherein the two guide elements are spaced with a predetermined interval between them along a side of and under the deodorizing and filtering unit and are fixed at one end to the bulkhead, and at the other end to a structure in the bottom of the space for deodorizing and filtering the exhaust gas.

6. The apparatus for collecting smoke and dust with a deodorizing function of claim 3, further comprising an acoustic absorption member disposed at an inner wall of the space for discharging exhaust gas, wherein the acoustic absorption member extends towards the driving motor of the air blower.

7. The apparatus for collecting smoke and dust with a deodorizing function of claim 6, wherein the acoustic absorption member is disposed at the inner wall of the space for discharging exhaust gas across an exhaust opening therein.

8. The apparatus for collecting smoke and dust with a deodorizing function of claim 6, wherein the acoustic absorption member has a V-shaped configuration.

9. The apparatus for collecting smoke and dust with a deodorizing function of claim 6, wherein the acoustic absorption member is covered by an acoustic insulating material.

10. The apparatus for collecting smoke and dust with a deodorizing function of claim 6,
wherein the deodorizing and filtering unit includes
the filtering means having a cylindrical shape,
the deodorizing means concentrically disposed at an outer side of the filtering means, and
cover plates disposed at both sides of the filtering means and the deodorizing means.

11. An apparatus for collecting smoke and dust with a deodorizing function, comprising:
a housing having a space for deodorizing and filtering exhaust gas and a space for discharging exhaust gas, wherein the space for deodorizing and filtering and the space for discharging are separated by a bulkhead having an opening,
a deodorizing and filtering unit provided with a filtering means having a cylindrical shape and a first deodorizing means concentrically disposed at an outer side of the filtering means, wherein the deodorizing and filtering unit is located at the opening of the bulkhead in the space for deodorizing and filtering the exhaust gas,
a vacuuming means located at the opening of the bulkhead for pulling exhaust gas that has passed through the deodorizing and filtering unit through the opening and discharging the exhaust gas through an exhaust portion thereof into the space for discharging the exhaust gas, and
a control panel for controlling the vacuuming means,
wherein the deodorizing and filtering unit is supported and held in the housing by a fastening member that passes through a hollow of the cylindrical filtering means and two guide elements that are located in the housing along a side of the deodorizing and filtering unit,
wherein the space for discharging the exhaust gas has an exhaust opening in a wall of the housing for discharging the exhaust gas to an outside of the housing,
wherein in a pathway for discharging the exhaust gas from the exhaust portion of the vacuuming means to the exhaust opening for discharging the exhaust gas, the exhaust portion is in communication with an exhaust pocket, and
wherein a second deodorizing means also having a noise absorbing function is adjacently located at a downstream side of the exhaust pocket.

12. The apparatus for collecting smoke and dust with a deodorizing function of claim 11, wherein the second deodorizing means has a two-layered structure including a deodorizing means and a filtering means.

13. The apparatus for collecting smoke and dust with a deodorizing function of claim 1 or 11,
wherein the deodorizing means is a perforated material having an inner wall and an outer wall, and a deodorizer is located between the inner wall and the outer wall.

14. The apparatus for collecting smoke and dust with a deodorizing function of claim 13,
wherein the perforated material is a net made from a resin.

15. The apparatus for collecting smoke and dust with a deodorizing function of claim 13,
wherein the deodorizer is activated charcoal.

16. The apparatus for collecting smoke and dust with a deodorizing function of claim 15,
wherein the activated charcoal is made from palm nuts, is ground, and has an irregular form of 1-6 mm in size, and has a specific surface area of more than 1,000 m$^2$/g.

17. The apparatus for collecting smoke and dust with a deodorizing function of claim 5,
wherein the activated charcoal is impregnated with an impregnating agent.

18. The apparatus for collecting smoke and dust with a deodorizing function of claim 17,
wherein the impregnating agent is an organic or inorganic substance that affects a specific odoriferous substance.

* * * * *

UNITED STATES PATENT AND TRADEMARK OFFICE
CERTIFICATE OF CORRECTION

| | | |
|---|---|---|
| PATENT NO. | : 7,887,623 B2 | Page 1 of 1 |
| APPLICATION NO. | : 11/887886 | |
| DATED | : February 15, 2011 | |
| INVENTOR(S) | : Keisuke Takayangi et al. | |

It is certified that error appears in the above-identified patent and that said Letters Patent is hereby corrected as shown below:

Claim 17, col. 14, line 35, "claim 5" should read --claim 15--.

Signed and Sealed this
Twenty-second Day of January, 2013

David J. Kappos
*Director of the United States Patent and Trademark Office*